(12) United States Patent
Brock et al.

(10) Patent No.: US 8,007,511 B2
(45) Date of Patent: Aug. 30, 2011

(54) SURGICAL INSTRUMENT DESIGN

(75) Inventors: David L. Brock, Natick, MA (US); Woojin Lee, Hopkinton, MA (US)

(73) Assignee: Hansen Medical, Inc., Mountain View, CA (US)

( * ) Notice: Subject to any disclaimer, the term of this patent is extended or adjusted under 35 U.S.C. 154(b) by 1092 days.

(21) Appl. No.: 10/858,822

(22) Filed: Jun. 1, 2004

(65) Prior Publication Data

US 2005/0049580 A1    Mar. 3, 2005

Related U.S. Application Data

(60) Provisional application No. 60/476,344, filed on Jun. 6, 2003.

(51) Int. Cl.
  *A61B 17/29* (2006.01)
(52) U.S. Cl. ...................................... 606/205
(58) Field of Classification Search .......... 606/130, 606/170, 205, 206–208, 210, 211; 901/15, 901/28, 29
  See application file for complete search history.

(56) References Cited

U.S. PATENT DOCUMENTS

| | | |
|---|---|---|
| 2,819,111 A | 1/1958 | Cozzens |
| 2,978,118 A | 4/1961 | Goertz et al. |
| 3,587,872 A | 6/1971 | Pauly |
| 3,631,737 A | 1/1972 | Wells |
| 3,694,021 A | 9/1972 | Mullen |
| 3,866,966 A | 2/1975 | Skinner, II |
| 3,877,780 A | 4/1975 | Taylor |
| 3,976,206 A | 8/1976 | Flateau |
| 4,066,141 A | 1/1978 | Elvin |
| 4,218,173 A | 8/1980 | Coindet et al. |
| 4,233,837 A | 11/1980 | Canfield |
| 4,246,661 A | 1/1981 | Pinson |
| 4,259,876 A | 4/1981 | Belyanin et al. |
| 4,287,759 A | 9/1981 | Cooper |
| 4,566,843 A | 1/1986 | Iwatsuka et al. |
| 4,604,016 A | 8/1986 | Joyce |

(Continued)

FOREIGN PATENT DOCUMENTS

EP    0 683 016 A1    11/1995

(Continued)

OTHER PUBLICATIONS

Tokuji Okada, "Computer Control of Multijointed Finger System for Precise Object-Handling", May/Jun. 1982, IEEE Transactions on Systems, Man, and Cybernetics, vol. SMC-12, No. 3, pp. 289-299. (10 pages).

(Continued)

*Primary Examiner* — Ryan J Severson
(74) *Attorney, Agent, or Firm* — Vista IP Law Group LLP

(57) ABSTRACT

A surgical instrument system having an instrument member or shaft with a distal portion positionable through an incision of a patient to an internal site and for operation by a surgeon from outside the patient. A tool is carried at the distal end of the instrument shaft controlled by the surgeon in performing a procedure at an operative site of the patient. At least first and second turnable members are spacedly disposed along the instrument shaft distal portion, both disposed within the internal site, and each controlled from outside the patient for providing at least respective first and second degrees of freedom of control of the tool. The turnable members may be either a pivot joint or a bendable section.

22 Claims, 8 Drawing Sheets

U.S. PATENT DOCUMENTS

| | | | |
|---|---|---|---|
| 4,655,673 A | 4/1987 | Hawkes | |
| 4,784,010 A | 11/1988 | Wood et al. | |
| 4,806,066 A | 2/1989 | Rhodes et al. | |
| 4,854,808 A | 8/1989 | Bruno | |
| 4,865,376 A | 9/1989 | Leaver et al. | |
| 4,883,400 A | 11/1989 | Kuban et al. | |
| 4,903,536 A | 2/1990 | Salisbury, Jr. et al. | |
| 4,921,293 A | 5/1990 | Ruoff et al. | |
| 4,967,126 A | 10/1990 | Gretz et al. | |
| 4,979,949 A | 12/1990 | Matsen, III et al. | |
| 5,038,089 A | 8/1991 | Szakaly | |
| 5,046,375 A | 9/1991 | Salisbury, Jr. et al. | |
| 5,078,140 A | 1/1992 | Kwoh | |
| 5,086,401 A | 2/1992 | Glassman et al. | |
| 5,105,367 A | 4/1992 | Tsuchihashi et al. | |
| 5,114,300 A | 5/1992 | Shahinpoor et al. | |
| 5,116,180 A | 5/1992 | Fung et al. | |
| 5,154,717 A | 10/1992 | Matsen, III et al. | |
| 5,184,601 A | 2/1993 | Putnam | |
| 5,193,963 A | 3/1993 | McAffee et al. | |
| 5,207,114 A | 5/1993 | Salisbury, Jr. et al. | |
| 5,217,003 A | 6/1993 | Wilk | |
| 5,236,432 A | 8/1993 | Matsen, III et al. | |
| 5,238,005 A | 8/1993 | Imran | |
| 5,266,875 A | 11/1993 | Slotine et al. | |
| 5,299,288 A | 3/1994 | Glassman et al. | |
| 5,327,790 A | 7/1994 | Levin et al. | |
| 5,339,799 A | 8/1994 | Kami et al. | |
| 5,350,355 A | 9/1994 | Sklar | |
| 5,368,015 A | 11/1994 | Wilk | |
| 5,372,147 A | 12/1994 | Lathrop, Jr. et al. | |
| 5,381,782 A * | 1/1995 | DeLaRama et al. | 600/149 |
| 5,382,885 A | 1/1995 | Salcudean et al. | |
| 5,397,323 A | 3/1995 | Taylor et al. | |
| 5,398,691 A | 3/1995 | Martin | |
| 5,402,801 A | 4/1995 | Taylor | |
| 5,410,638 A | 4/1995 | Colgate et al. | |
| 5,417,210 A | 5/1995 | Funda et al. | |
| 5,430,643 A | 7/1995 | Seraji | |
| 5,477,856 A | 12/1995 | Lundquist | |
| 5,492,131 A | 2/1996 | Galel | |
| 5,515,478 A | 5/1996 | Wang | |
| 5,524,180 A | 6/1996 | Wang et al. | |
| 5,540,649 A * | 7/1996 | Bonnell et al. | 600/114 |
| 5,553,198 A | 9/1996 | Wang et al. | |
| 5,572,999 A | 11/1996 | Funda et al. | |
| 5,587,937 A | 12/1996 | Massie et al. | |
| 5,618,294 A | 4/1997 | Aust et al. | |
| 5,619,180 A | 4/1997 | Massimino et al. | |
| 5,624,398 A | 4/1997 | Smith et al. | |
| 5,625,576 A | 4/1997 | Massie et al. | |
| 5,626,595 A | 5/1997 | Sklar et al. | |
| 5,631,973 A | 5/1997 | Green | |
| 5,632,758 A | 5/1997 | Sklar | |
| 5,649,956 A | 7/1997 | Jensen et al. | |
| 5,657,429 A | 8/1997 | Wang et al. | |
| 5,713,946 A | 2/1998 | Ben-Haim | |
| 5,738,096 A | 4/1998 | Ben-Haim | |
| 5,749,362 A | 5/1998 | Funda | |
| 5,754,741 A | 5/1998 | Wang et al. | |
| 5,762,458 A | 6/1998 | Wang et al. | |
| 5,784,542 A | 7/1998 | Ohm | |
| 5,792,135 A * | 8/1998 | Madhani et al. | 606/1 |
| 5,800,333 A | 9/1998 | Liprie | |
| 5,800,423 A | 9/1998 | Jensen | |
| 5,807,377 A | 9/1998 | Madhani et al. | |
| 5,807,378 A | 9/1998 | Jensen et al. | |
| 5,808,665 A | 9/1998 | Green | |
| 5,810,880 A | 9/1998 | Jensen et al. | |
| 5,814,038 A | 9/1998 | Jensen et al. | |
| 5,815,640 A | 9/1998 | Wang et al. | |
| 5,817,084 A | 10/1998 | Jensen | |
| 5,821,920 A | 10/1998 | Rosenberg et al. | |
| 5,825,982 A | 10/1998 | Wright et al. | |
| 5,828,197 A | 10/1998 | Martin et al. | |
| 5,833,608 A | 11/1998 | Acker | |
| 5,833,656 A | 11/1998 | Smith et al. | |
| 5,843,076 A | 12/1998 | Webster | |
| 5,855,553 A | 1/1999 | Tajima et al. | |
| 5,855,583 A | 1/1999 | Wang et al. | |
| 5,876,325 A * | 3/1999 | Mizuno et al. | 600/102 |
| 5,878,193 A | 3/1999 | Wang et al. | |
| 5,907,664 A | 5/1999 | Wang et al. | |
| 5,931,832 A | 8/1999 | Jensen | |
| 5,950,629 A | 9/1999 | Taylor | |
| 5,954,692 A | 9/1999 | Smith et al. | |
| 5,971,976 A | 10/1999 | Wang et al. | |
| 5,976,122 A | 11/1999 | Madhani et al. | |
| 6,001,108 A | 12/1999 | Wang et al. | |
| 6,007,550 A | 12/1999 | Wang et al. | |
| 6,024,695 A | 2/2000 | Taylor et al. | |
| 6,036,636 A | 3/2000 | Motoki et al. | |
| 6,063,095 A | 5/2000 | Wang et al. | |
| 6,080,181 A | 6/2000 | Jensen et al. | |
| 6,083,170 A | 7/2000 | Shlomo | |
| 6,096,004 A | 8/2000 | Meglan et al. | |
| 6,102,850 A | 8/2000 | Wang et al. | |
| 6,106,511 A | 8/2000 | Jensen | |
| 6,120,433 A | 9/2000 | Mizuno et al. | |
| 6,132,368 A | 10/2000 | Cooper | |
| 6,132,441 A | 10/2000 | Grace | |
| 6,197,017 B1 * | 3/2001 | Brock et al. | 606/1 |
| 6,206,903 B1 | 3/2001 | Ramans | |
| 6,213,565 B1 | 4/2001 | Hart | |
| 6,223,100 B1 * | 4/2001 | Green | 700/264 |
| 6,233,476 B1 | 5/2001 | Strommer | |
| 6,233,504 B1 | 5/2001 | Das et al. | |
| 6,246,200 B1 | 6/2001 | Blumenkranz et al. | |
| 6,266,551 B1 | 7/2001 | Osadchy | |
| 6,272,371 B1 | 8/2001 | Shlomo | |
| 6,290,675 B1 | 9/2001 | Vujanic et al. | |
| 6,309,397 B1 | 10/2001 | Julian et al. | |
| 6,312,435 B1 | 11/2001 | Wallace et al. | |
| 6,325,808 B1 | 12/2001 | Bernard et al. | |
| 6,331,181 B1 | 12/2001 | Tierney et al. | |
| 6,346,072 B1 | 2/2002 | Cooper | |
| 6,364,888 B1 | 4/2002 | Niemeyer et al. | |
| 6,370,411 B1 | 4/2002 | Osadchy | |
| 6,371,907 B1 | 4/2002 | Hasegawa et al. | |
| 6,371,952 B1 | 4/2002 | Madhani | |
| 6,375,471 B1 | 4/2002 | Wendlandt | |
| 6,377,011 B1 | 4/2002 | Ben-Ur | |
| 6,385,509 B2 | 5/2002 | Das et al. | |
| 6,393,340 B2 | 5/2002 | Funda | |
| 6,394,998 B1 | 5/2002 | Wallace et al. | |
| 6,398,726 B1 | 6/2002 | Ramans et al. | |
| 6,400,979 B1 | 6/2002 | Stoianovici | |
| 6,413,264 B1 | 7/2002 | Jensen et al. | |
| 6,424,885 B1 | 7/2002 | Niemeyer | |
| 6,432,112 B2 | 8/2002 | Brock et al. | |
| 6,436,107 B1 | 8/2002 | Wang et al. | |
| 6,441,577 B2 | 8/2002 | Blumenkranz et al. | |
| 6,451,027 B1 | 9/2002 | Cooper et al. | |
| 6,459,926 B1 | 10/2002 | Nowlin et al. | |
| 6,461,372 B1 | 10/2002 | Jensen et al. | |
| 6,463,361 B1 | 10/2002 | Wang et al. | |
| 6,468,265 B1 | 10/2002 | Evans et al. | |
| 6,490,490 B1 | 12/2002 | Uchikubo et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,496,099 B2 | 12/2002 | Wang et al. | |
| 6,517,565 B1 | 2/2003 | Whitman et al. | |
| 6,522,906 B1 | 2/2003 | Salisbury, Jr. et al. | |
| 6,554,844 B2 | 4/2003 | Lee et al. | |
| 6,565,554 B1 | 5/2003 | Niemeyer | |
| 6,569,084 B1 | 5/2003 | Mizuno | |
| 6,574,355 B2 | 6/2003 | Green | |
| 6,587,750 B2 | 7/2003 | Gerbi et al. | |
| 6,594,552 B1 | 7/2003 | Nowlin et al. | |
| 6,610,007 B2 | 8/2003 | Belson | |
| 6,620,173 B2 | 9/2003 | Gerbi et al. | |
| 6,620,174 B2 | 9/2003 | Jensen et al. | |
| 6,626,899 B2 | 9/2003 | Houser | |
| 6,645,196 B1 | 11/2003 | Nixon et al. | |
| 6,659,939 B2 | 12/2003 | Moll | |
| 6,676,684 B1 | 1/2004 | Morley et al. | |

| | | |
|---|---|---|
| 6,685,698 B2 | 2/2004 | Morley et al. |
| 6,692,485 B1 | 2/2004 | Brock et al. |
| 6,699,235 B2 | 3/2004 | Wallace et al. |
| 6,720,988 B1 | 4/2004 | Gere et al. |
| 6,726,675 B1 | 4/2004 | Beyar |
| 6,726,699 B1 | 4/2004 | Wright et al. |
| 6,728,599 B1 | 4/2004 | Wang et al. |
| 6,770,081 B1 | 8/2004 | Cooper et al. |
| 6,783,524 B2 | 8/2004 | Anderson et al. |
| 6,788,018 B1 | 9/2004 | Blumenkranz |
| 6,793,653 B2 | 9/2004 | Sanchez et al. |
| 6,799,065 B1 | 9/2004 | Niemeyer |
| 6,804,581 B2 | 10/2004 | Wang et al. |
| 6,817,972 B2 | 11/2004 | Snow |
| 6,817,974 B2 | 11/2004 | Cooper et al. |
| 6,837,883 B2 | 1/2005 | Moll et al. |
| 6,840,938 B1 | 1/2005 | Morley et al. |
| 6,852,107 B2 | 2/2005 | Wang et al. |
| 6,858,003 B2 | 2/2005 | Evans |
| 6,860,877 B1 | 3/2005 | Sanchez et al. |
| 6,905,460 B2 | 6/2005 | Wang |
| 6,911,916 B1 | 6/2005 | Wang et al. |
| 6,936,001 B1 | 8/2005 | Snow |
| 6,951,535 B2 | 10/2005 | Ghodoussi et al. |
| 6,963,792 B1 | 11/2005 | Green |
| 6,994,708 B2 | 2/2006 | Manzo |
| 7,021,173 B2 | 4/2006 | Stoianovici |
| 7,025,064 B2 | 4/2006 | Wang et al. |
| 7,074,179 B2 | 7/2006 | Wang |
| 7,087,049 B2 | 8/2006 | Nowlin |
| 7,169,141 B2 | 1/2007 | Brock |
| 7,297,142 B2 | 11/2007 | Brock |
| 7,320,700 B2 | 1/2008 | Cooper |
| 7,331,967 B2 | 2/2008 | Lee |
| 7,343,195 B2 | 3/2008 | Strommer |
| 7,371,210 B2 | 5/2008 | Brock |
| 2001/0031983 A1 * | 10/2001 | Brock et al. ................ 606/205 |
| 2003/0135204 A1 | 7/2003 | Lee |
| 2004/0034282 A1 | 2/2004 | Quaid |
| 2004/0034365 A1 | 2/2004 | Lentz |
| 2005/0131460 A1 | 6/2005 | Gifford, III |
| 2006/0200049 A1 | 9/2006 | Leo |
| 2007/0060847 A1 | 3/2007 | Leo |
| 2007/0060879 A1 | 3/2007 | Lee |
| 2007/0123851 A1 | 5/2007 | Alejandro |
| 2007/0287999 A1 | 12/2007 | Malecki |
| 2007/0293724 A1 | 12/2007 | Saadat |
| 2007/0299434 A1 | 12/2007 | Malecki |
| 2008/0009750 A1 | 1/2008 | Aeby |
| 2008/0015445 A1 | 1/2008 | Saadat |
| 2008/0300592 A1 | 12/2008 | Weitzner |

FOREIGN PATENT DOCUMENTS

| | | |
|---|---|---|
| EP | 0 776 738 A2 | 6/1997 |
| JP | 06114000 | 4/1994 |
| WO | WO 98/25666 | 6/1998 |
| WO | WO 00/60421 | 10/2000 |
| WO | WO 00/60521 | 10/2000 |
| WO | WO 00/67640 | 11/2000 |
| WO | WO 02/74178 | 2/2002 |
| WO | WO 03/091839 | 6/2003 |

OTHER PUBLICATIONS

Ikuta, et al., "Shape Memory Alloy Servo Actuator System With Electric Resistance Feedback and Application for Active Endoscope", 1988 IEEE, CH2555-1/88/0000/0427-430. (4 pages).

M.W. Thring, "Robots And Telechirs: Manipulators With Memory; Remote Manipulators; Machine Limbs For The Handicapped", First published in 1983 by Ellis Horwood Limited. (81 pages).

Tokuji Okada, "A Versatile End-Effector With Flexible Fingers", Winter 1979, Robotics Age, pp. 31-39, 4 pages.

David Cassak, "R2D2 in the OR", Start-Up, May 1997, 16 pages.

David Allen et al., "Telesurgery: Telementoring, Telepresence, Telerobotics, The NeuroLink Experience", Telemedicine Today (Program Survey), vol. 5, issue 3, published Apr. 1997, 8 pages.

* cited by examiner

SURGICAL INSTRUMENT DESIGN

RELATED APPLICATIONS

This application claims the benefit of U.S. Provisional Application No. 60/476,344, filed on Jun. 6, 2003. The entire teachings of the above application are incorporated herein by reference.

BACKGROUND OF THE INVENTION

Just as the unique curved guide tube concepts represent an improvement over past systems, particularly ones using a "center-of-rotation" of the instrument at the incision, the concepts set forth herein represent still other improvements by further minimizing the rotation or pivoting at the incision. In some embodiments described herein only rotation occurs at the incision and no pivoting. Such pivoting causes stress at the incision and can damage tissue. In other embodiments described herein neither pivoting, rotation nor translation occur at the incision.

SUMMARY OF THE INVENTION

The systems that are described herein use a novel combination of internal (of the patient) degrees-of-freedom to achieve a fully articulated telesurgical instrument system. Unlike traditional telesurgical systems, which use complex and heavy robotic arm assemblies to simulate human movement, the systems described herein preferably use a combination of internal and external motions, preferably with the remote and stationary location of motors.

In accordance with one aspect of the invention there is provided a system that includes an instrument member or instrument shaft that includes, internally of the incision, two degrees-of-motion members, one that can be referred to as a "wrist" member or wrist turnable member disposed proximal of the distal end effector of the instrument, and another that can be referred to as a "elbow" or elbow turnable member, disposed proximal of the wrist member. These turnable members are to be remotely controlled from a master interface device to control the disposition of the end effector. These turnable members may be implemented by a pivot joint or a bendable section of the instrument shaft. For a pivot joint, in addition to one degree of freedom by pivoting at the wrist, one degree of freedom by pivoting at the elbow, two degrees of freedom at the end effector, there may also be provided rotation of the instrument shaft, linear translation of the instrument shaft and rotation of a forearm member that is disposed between the wrist and elbow members. This provides 7 DOF (Degrees Of Freedom), while providing only rotation and linear translation in the area of the incision, but no pivoting thereat. In essence, motions at the incision are replaced by motions that are internal of the patient.

If the turnable member is a bendable section of the instrument shaft this can be controlled in a manner similar to the pivot joint to provide only one degree of freedom thereat, or alternatively, each bendable section may have two degrees of freedom by orthogonal control at the bendable section. This may be implemented to provide more than 7 DOF for the instrument system, or alternatively, the extra degrees of freedom at the bendable section can be used to substitute for other motions. For example, with the use of one or more bendable sections, one can then provide an instrument shaft that neither rotates nor transitions linearly, thus, in essence, providing all degrees of freedom internal of the incision.

In accordance with a further aspect of the invention there may additionally be provided a "shoulder" member or shoulder turnable member disposed proximal of the elbow member. For this arrangement the "shoulder" member provides a degree of freedom and thus the instrument shaft only has one degree of freedom, namely rotation thereof. In this embodiment the shoulder turnable member may also be formed either as a pivot joint or as a bendable section.

In accordance with another aspect of the invention there is provided a surgical instrument system that includes an instrument member having a distal portion positionable through an incision of a patient to an internal site and for operation by a surgeon from outside the patient; a tool carried at the distal end of the instrument member controlled by the surgeon in performing a procedure at an operative site of the patient; and at least first and second turnable members disposed along the instrument member distal portion, both disposed within the internal site, and each controlled from outside the patient and for providing at least respective first and second degrees of freedom of control of the tool. Each turnable member may comprise a remotely controllable pivot connection, or alternatively each turnable member may comprise a remotely controllable bendable section. Also, a third turnable member may be provided at an internal location, essentially substituting for one of the degrees of freedom at the incision.

BRIEF DESCRIPTION OF THE DRAWINGS

The following are drawings of several different embodiments that are considered as falling within the scope of the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

The present invention, is related to co-pending U.S. patent application Ser. No. 10/299,588 filed Nov. 18, 2002; co-pending U.S. patent application Ser. No. 10/012,845 filed on Nov. 16, 2001 and published as U.S. Publication No. 2002/0128633 on Sep. 12, 2002 and co-pending U.S. patent application Ser. No. 10/302,804 filed Nov. 21, 2002, the entire teachings of which are incorporated herein by reference.

Any reference to figure numbers herein pertains to the above list of drawings that are attached hereto. Reference to any other figure numbers will be by identification as to the co-pending application in which the figure appears.

Figure 1:
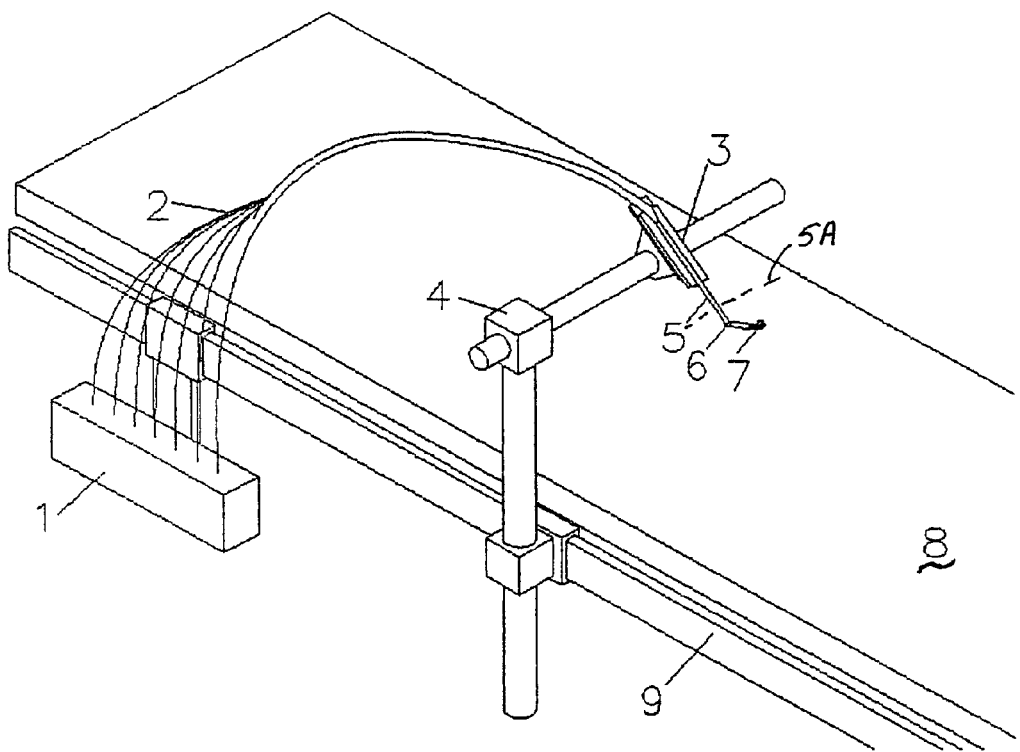
FIG. 1 is a perspective view of one embodiment of the invention using an internal wrist and elbow.

FIG. 1 is a perspective view of one embodiment of the invention using an internal wrist and elbow. This view depicts a motor array or pack 1 mounted to a surgical table 8. The motor array may be supported from the table rail 9, and is usually disposed outside the sterile field. A plurality of cables in conduits 2 are driven by the respective motors of the motor array 1. Further details of the motor array and cabling are included in U.S. patent application Ser. No. 10/012,845 and in particular FIGS. 8E through 8L, and the associated descriptions on pages 16 and 17. As described there, the cabling 2 may be detachably coupled with the motor pack 1, so that the slave unit (slider 3, etc.) is readily detachable from both the support bracket 4, as well as the motor pack 1. This makes the slave unit readily portable, and is relatively light in weight.

A linear slider 3 (which may also be referred to as a carriage) is mounted on a static fixture or bracket 4. The slider 3 supports the instrument shaft or stem 5. The instrument stem 5 is inserted into the patient through an incision formed during a minimally invasive procedure. The instrument stem is positioned so that the incision is at a location somewhere between the distal end of the slider 3 and the elbow joint 6. Refer in FIG. 1 to the dotted line 5A indicative of the possible location of the incision in the patient. For further details of the slider 3 refer to U.S. patent application Ser. No. 10/012,845, such as in FIGS. 8F, 11 and 15 illustrating the adaptor 15 including the carriage 226 forming a slider arrangement.

In FIG. 1 herein, the elbow joint 6 articulates a pivotal motion inside the patient's body, as will be described in further detail in FIG. 2. FIG. 1 also illustrates the end effector 7 that is controllable with pitch, yaw, and roll rotation, as well as a gripping motion by the end effector. A wrist 11, shown in somewhat more detail in FIG. 2, is used just proximal of the end effector jaws to provide the desired degrees of freedom.

For further details of the structures schematically depicted in FIG. 1 refer to details shown in U.S. patent application Ser. No. 10/012,845. In U.S. patent application Ser. No. 10/012,845 refer to FIGS. 8-11, and associated descriptive text on pages 15 and 17-19. This supporting description shows a carriage 226 in FIGS. 8-11 that functions as a slider for carrying the instrument. The instrument stem may be like that shown in FIG. 15A by instrument 16. FIG. 16 also shows various versions of end effectors including a wrist pivot joint in FIGS. 16A-16D and bendable sections in FIGS. 16E-16K, along with accompanying text descriptions. Also refer to U.S. patent application Ser. No. 10/299,588 for further descriptions of end effectors and bendable sections, such as in FIGS. 26-48, and associated descriptions in the specification.

Figure 2:
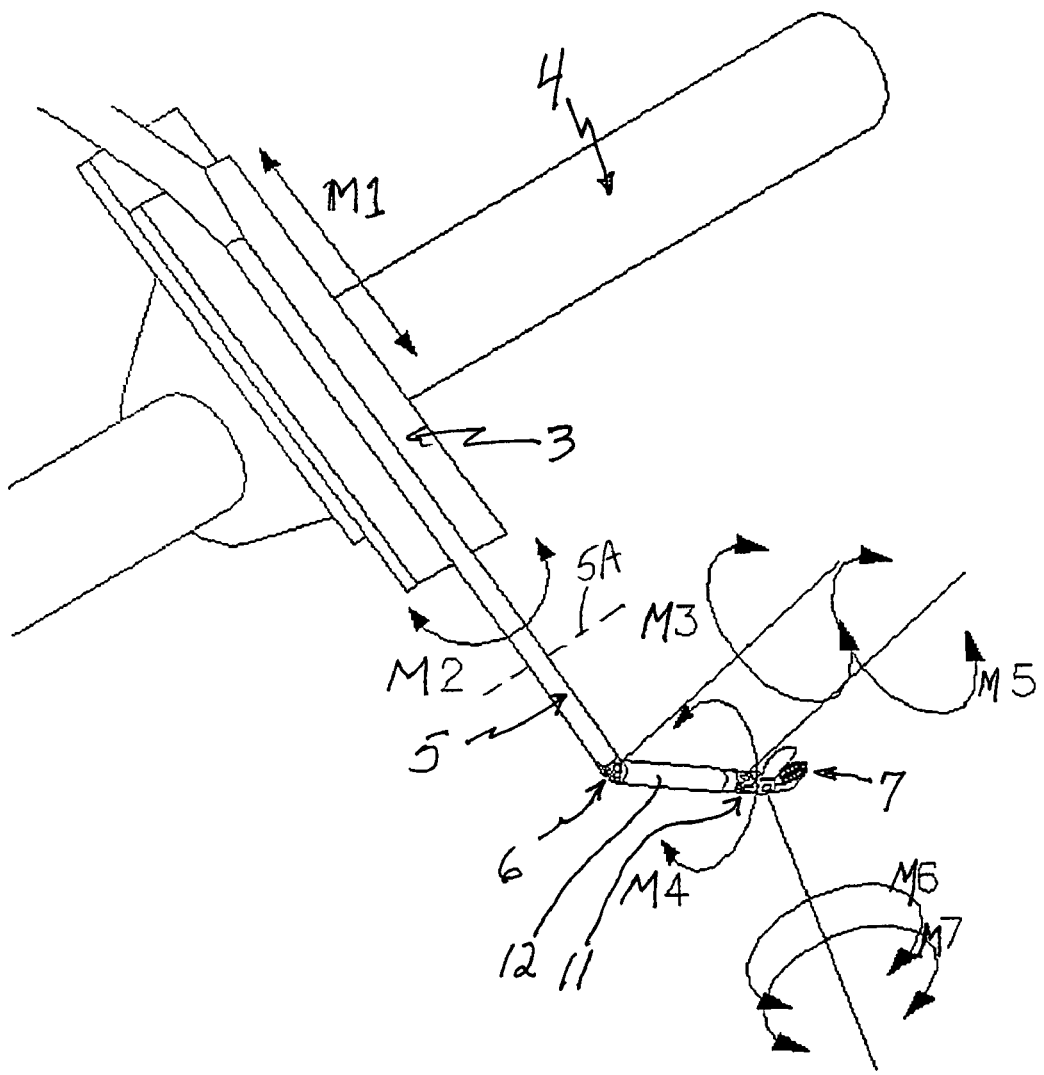
FIG. 2 is a schematic perspective view illustrating the degrees of freedom associated with the embodiment of FIG. 1.

Refer now to FIG. 2 for further details of the embodiment of FIG. 1. FIG. 2 shows, in particular, the degrees of freedom or motions of the instrument system. Motion M1 indicates the linear translation of the slider 3. Motion M2 indicates the axial rotation of the instrument stem 5 about its longitudinal axis. FIG. 2 also illustrates the elbow member or joint 6. This member provides pivotal motion within the patient. This joint itself may be substantially the same as the joint shown in U.S. patent application Ser. No. 10/012,845 in FIG. 16A. FIG. 2 also depicts the wrist joint 11 which also may be the same as described in U.S. patent application Ser. No. 10/012,845, such as in FIG. 16A or FIG. 16C. The joints 6 and 11 are intercoupled by the forearm member 12. The control cabling that operates the various degrees of freedom couples through the instrument stem 5, and one cable controls the rotation of the forearm member 12. Refer in FIG. 2 to the motion M3 indicating pivoting at the elbow 6 and the motion M4 indicating rotation of the forearm member 12 which, in turn, rotates the end effector 7. The forearm member 12 may thus have a rotational joint at its more proximal end, adjacent member 6, to facilitate motion M4.

In FIG. 2 there are also illustrated motions associated with the wrist and end effector. Motion M5 indicates yaw rotation at the wrist member 11. The motions M6 and M7 are remotely controlled at the end effector pivot axis to provide instrument pitch and grip (opening and closing of the end effector jaws).

Figure 3:
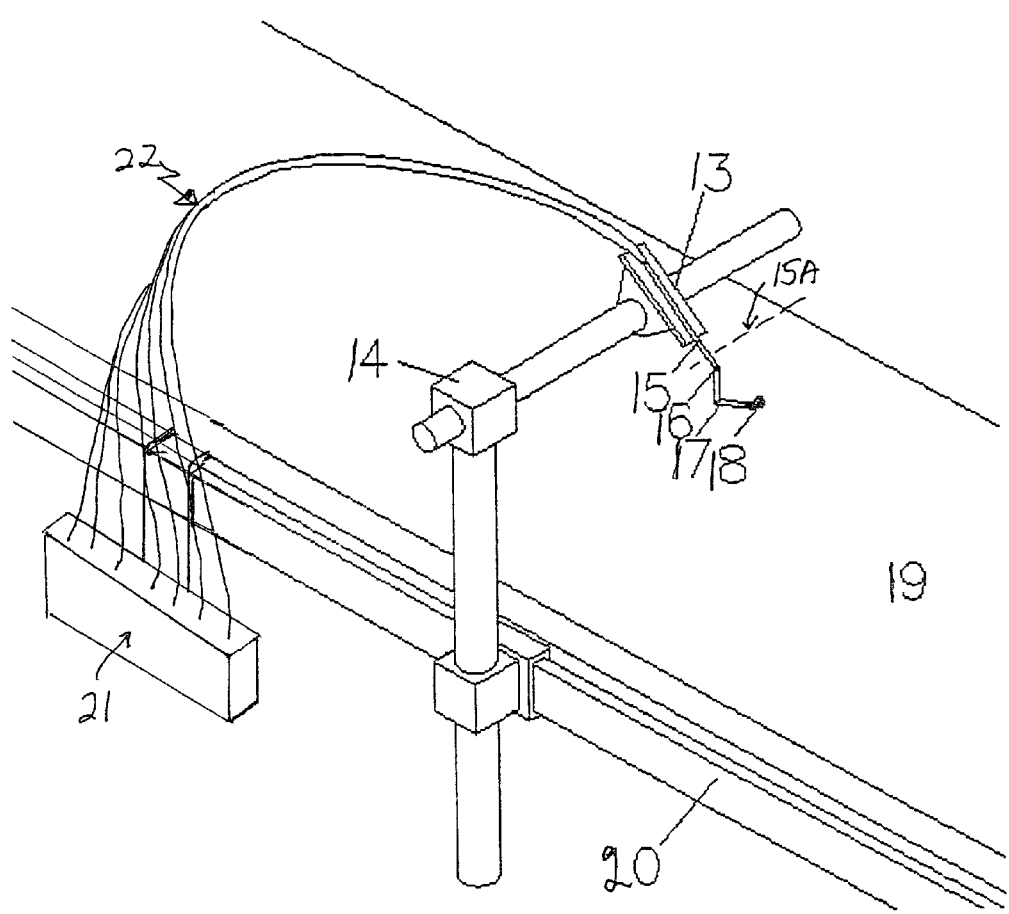
FIG. 3 is a perspective view of another embodiment of the invention using an internal wrist, elbow and shoulder.

FIG. 3 is a perspective view of another embodiment of the invention using an internal wrist, elbow and additionally a shoulder. This view depicts a motor array or pack 21 mounted to the surgical table 19. The motor array may be supported from the table rail 20, and is usually disposed outside the sterile field. A plurality of cables in conduits 22 are driven by the respective motors of the motor array 1. For further details of the motor array and cabling refer to U.S. patent application Ser. No. 10/012,845 and in particular FIGS. 8E through 8L, and the associated descriptions on pages 16 and 17. As described there, the cabling 22 may be detachably coupled with the motor pack 21, so that the slave unit (slider 13, etc.) is readily detachable from both the support bracket 14, as well as the motor pack 21. This makes the slave unit readily portable, and is light in weight.

A linear slider 13 is mounted on a static fixture or bracket 14. The slider 13 supports the instrument shaft or stem 15. The instrument stem 15 is inserted into the patient through an incision. The instrument stem is positioned so that the incision is at a location somewhere between the distal end of the slider 13 and the shoulder member or joint 16. Refer in FIG. 3 to the dotted line 15A indicative of the possible location of the incision in the patient. The shoulder member 16 and elbow member 17, in this particular version, articulate pivotal motions inside the patient's body, as will be described in further detail in conjunction with FIG. 4. FIG. 3 also illustrates the end effector 18 that is controllable with pitch, yaw, and roll rotation, as well as a gripping motion by the end effector. A wrist 23, shown in somewhat more detail in FIG. 4, is used just proximal of the end effector jaws to provide an additional degree of freedom.

For further details of the structures schematically depicted in FIG. 3 refer to previous descriptions referenced in U.S. patent application Ser. No. 10/012,845. In U.S. patent application Ser. No. 10/012,845 refer to FIGS. 8-11, and the associated descriptive text on pages 15 and 17-19. This supporting description shows a carriage 226 in FIGS. 8-11 that functions as a slider for carrying the instrument. The instrument stem may be like that shown in FIG. 15A by instrument 16. FIG. 16 also shows various versions of end effectors including a wrist pivot joint in FIGS. 16A-16D and bendable sections in FIGS. 16E-16K, along with accompanying text descriptions. Also refer to U.S. patent application Ser. No. 10/299,588 for further descriptions of end effectors and bendable sections, such as in FIGS. 26-48, and associated descriptions in the specification. These disclosed members may be used for any one of the wrist, elbow or shoulder members of FIGS. 3 and 4.

Figure 4:
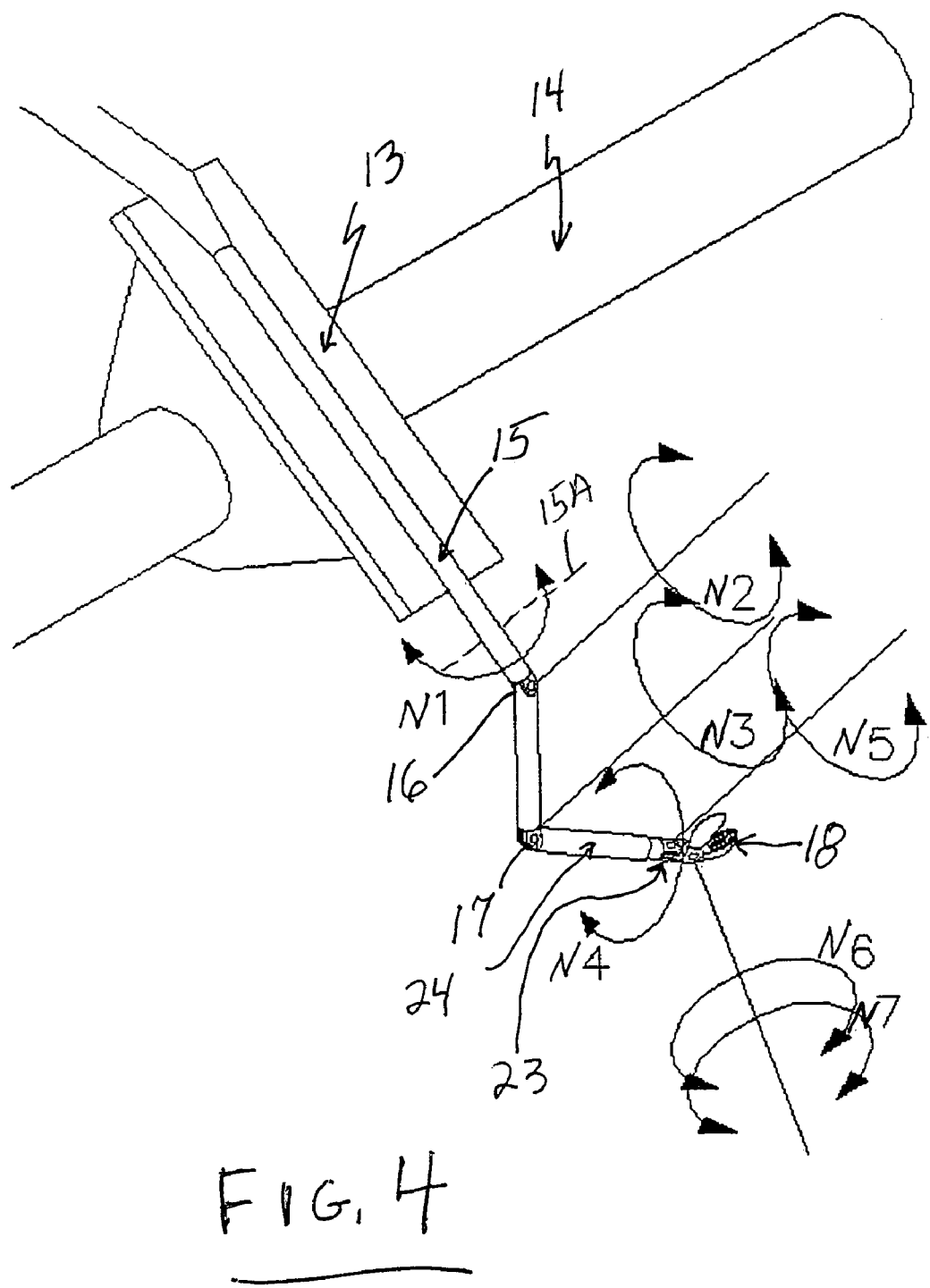
FIG. 4 is a schematic perspective view illustrating the degrees of freedom associated with the embodiment of FIG. 3.

Refer now to FIG. 4 for further details of the embodiment of FIG. 3. FIG. 4 shows, in particular, the degrees of freedom or motions of the instrument system. It is noted in FIG. 4 that there is no linear translation at the incision due to the addition of the shoulder member 16. Motion N1 indicates axial rotation of the instrument stem 15 about its longitudinal axis.

Motion N2 indicates the motion at the added internal shoulder joint 16. FIG. 4 also illustrates the elbow member or joint 17. Both of the joints 16 and 17 provide pivotal motion within the patient. Both of these joints may be a pivot joint as depicted in U.S. patent application Ser. No. 10/012,845, FIG. 16, or as described later, these motions may be implemented by bendable sections of the instrument shaft. FIG. 4 also depicts the wrist joint 23 which also may be the same as described in U.S. patent application Ser. No. 10/012,845, such as in FIG. 16A or FIG. 16C. The joints 17 and 23 are intercoupled by the forearm member 24. The control cabling that operates the various degrees of freedom couples through the instrument stem 5, and one cable controls the rotation of the forearm member 24. Refer in FIG. 4 to the motion N3 indicating pivoting at the elbow 17 and the motion N4 indicating rotation of the forearm member 24 which, in turn, rotates the end effector 18. For the purpose of rotation of the forearm 24, there may be provided a rotational joint at the proximal end of the forearm 24 adjacent member 17.

In FIG. 4 there are also illustrated motions associated with the wrist and end effector. Motion N5 indicates yaw rotation at the wrist member 23. The motions N6 and N7 are remotely controlled at the end effector pivot axis to provide instrument pitch and grip (opening and closing of the end effector jaws).

In the two embodiments described so far, pivot joints are described. Reference has been made to U.S. patent application Ser. No. 10/012,845 for different versions of pivot joints, such as in FIGS. 16A and 16C. These same types of joints may also be used for the elbow and shoulder members, such as member 6 in FIG. 2 or members 16 and 17 in FIG. 4. All such joint members are controlled from cables running within the instrument shaft, and under control from a master station where a medical practitioner operates an input user interface device such as handle grips, a joystick, or other input control devices. In this regard refer to U.S. patent application Ser. No. 10/012,845 and FIG. 1 thereof showing an instrument system including master and slave sides, and FIG. 16A showing cables 606 and 607 that control that particular wrist joint. Similar cabling can be used to control other joints, all controlled from motors associated with the slave unit, and preferably disposed outside the sterile field as indicated in FIGS. 1 and 3.

Figure 5:
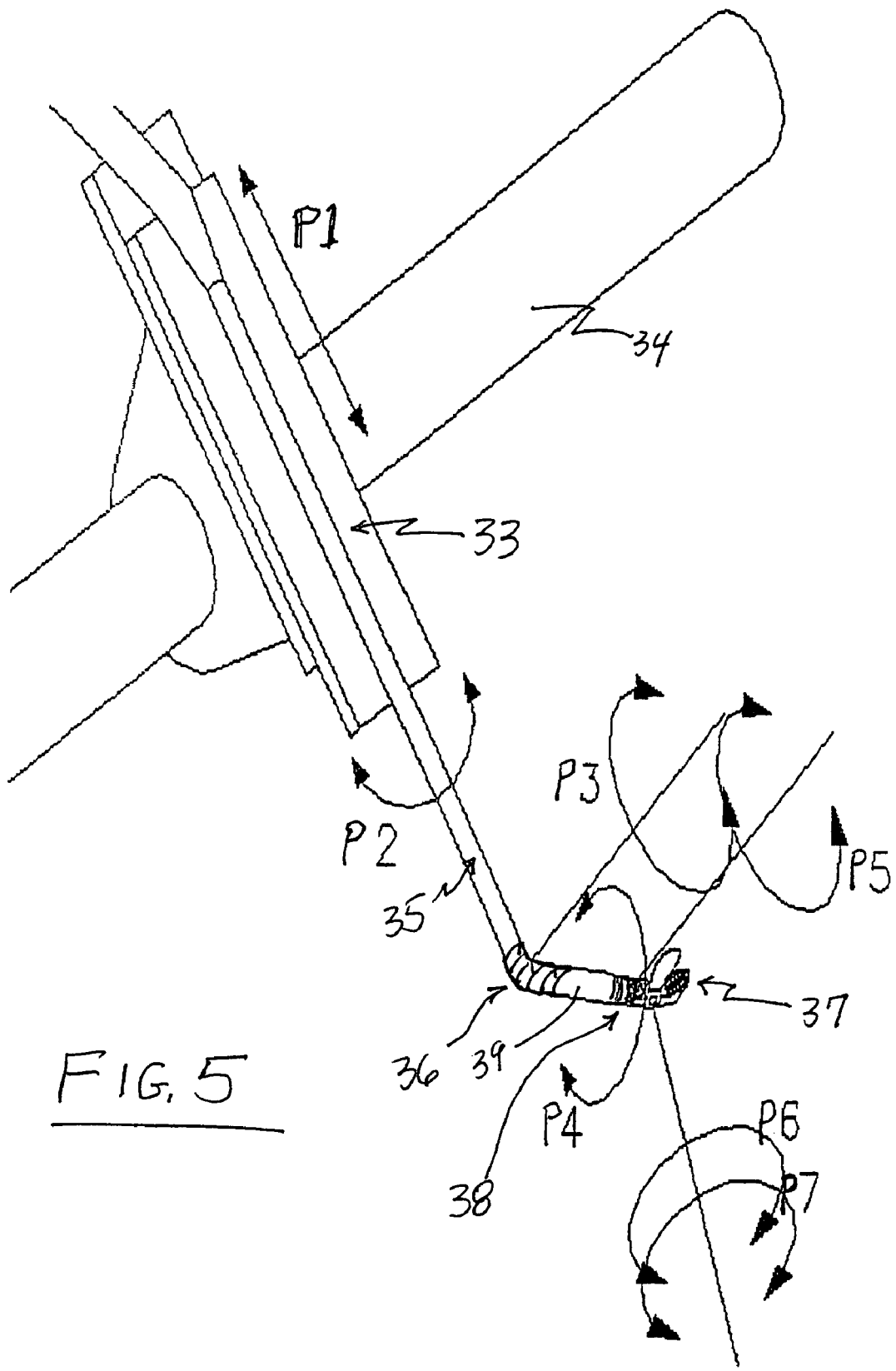
FIG. 5 is a schematic perspective view illustrating the degrees of freedom associated with an embodiment like that of FIG. 1, but using a bendable section instead of a pivot joint.
Figure 6:
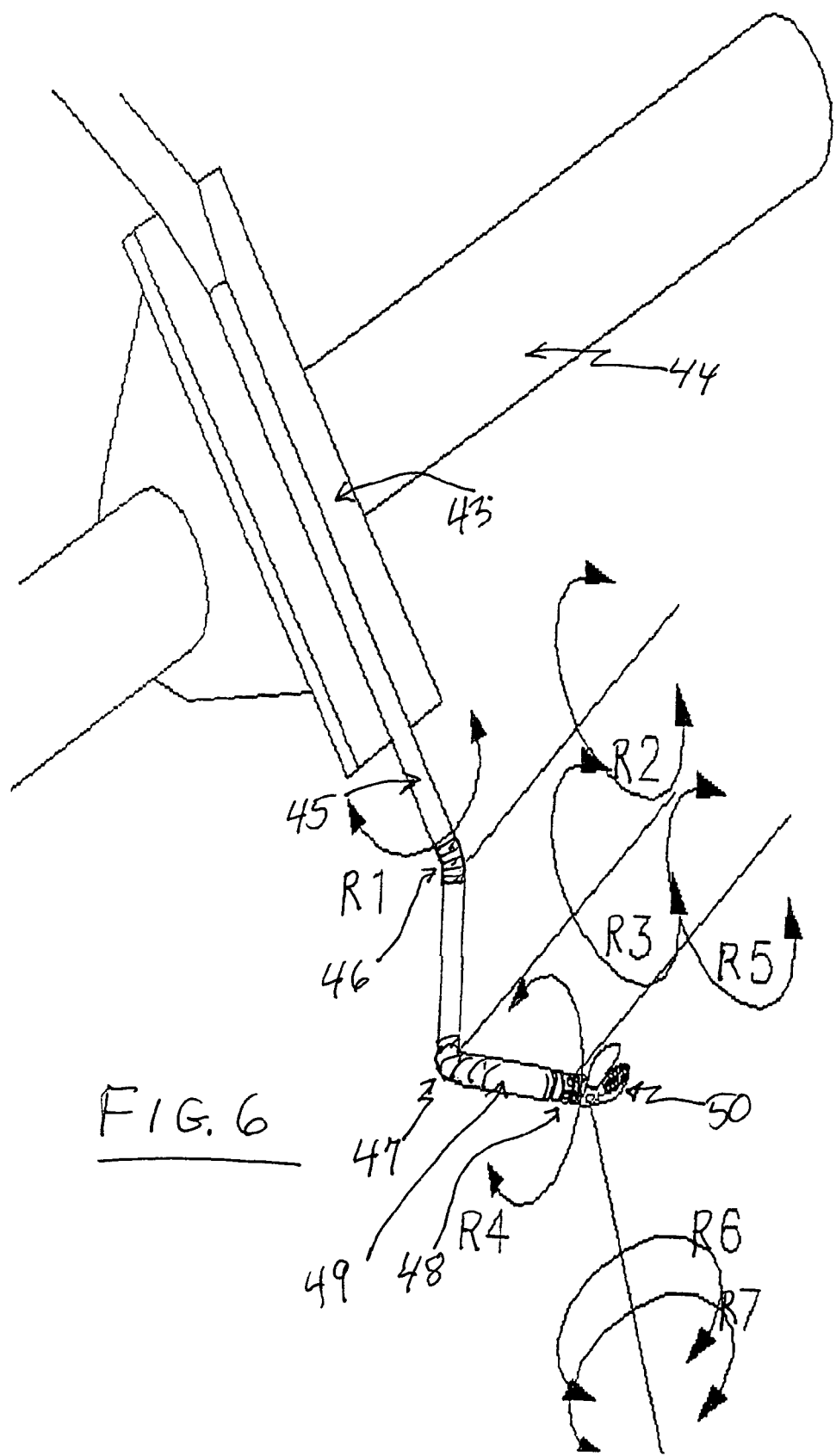
FIG. 6 is a schematic perspective view illustrating the degrees of freedom associated with an embodiment like that of FIG. 3, but using a bendable section instead of a pivot joint.

In FIGS. 1-4 all of the motions disclosed are implemented by pivot joints. However, in another embodiment of the invention these motions may be implemented by respective bendable sections. One advantage of a bendable section is that it can be constructed to provide two degrees of freedom while the pivot joint is limited to only a single degree of freedom about the pivot axis. For specific embodiments that may be used in implementing these bendable sections refer to U.S. patent application Ser. No. 10/299,588 and U.S. patent application Ser. No. 10/012,845. In particular, in U.S. patent application Ser. No. 10/299,588 in FIGS. 41-47 there is one example of a bendable section that may be used. These sections may be constructed using alternating ribs and slots configured to enable ready bending or flexing where they are located. This action is remotely controlled from a master input device such as in the manner described in U.S. patent application Ser. No. 10/299,588. U.S. patent application Ser. No. 10/299,588 also shows the control cabling used for actuation of the bendable sections. As indicated, one advantage to a bendable section is that it can be operated with two degrees of freedom by orthogonally disposed cable sets to provide bending in orthogonal directions, a characteristic not found in a pivot joint. FIGS. 5 and 6 describe the instrument system in this embodiment implemented using bendable sections.

Refer now to FIG. 5 for an illustration of the degrees of freedom or motions of the instrument system using bendable sections. In still other embodiments of the invention a combination of pivot joints and bendable sections may be used. In FIG. 5 motion P1 indicates the linear translation of the slider 33. Motion P2 indicates the axial rotation of the instrument stem 35 about its longitudinal axis. FIG. 5 also illustrates the elbow member 36, in the form of a bendable section, such as described in U.S. patent application Ser. No. 10/299,588 or U.S. patent application Ser. No. 10/012,845. This bendable section provides a bending, flexing or turning motion of the instrument stem within the patient. FIG. 5 also depicts the wrist member 38 which also may be the same as described in U.S. patent application Ser. No. 10/012,845, such as in FIG. 16E through FIG. 16K. The members 36 and 38 may be intercoupled by the forearm member 39. The control cabling that operates the various degrees of freedom couples through the instrument stem 35, and one cable may control the rotation of the forearm member 39. Refer in FIG. 5 to the motion P3 indicating bending at the elbow 36 and the motion P4 indicating rotation of the forearm member 39 which, in turn, rotates the end effector 37. The forearm member 39 may thus have a rotational joint at its more proximal end to facilitate motion P4.

In FIG. 5 there are also illustrated motions associated with the wrist and end effector. Motion P5 indicates yaw rotation or bending at the wrist member 38. The motions P6 and P7 are remotely controlled at the end effector pivot axis to provide instrument pitch and grip (opening and closing of the end effector jaws).

Refer now to FIG. 6 for further details of the degrees of freedom or motions of the instrument system that includes both elbow and shoulder members 46 and 47. Motion R1 indicates axial rotation of the instrument stem 45 about its longitudinal axis. Motion R2 indicates the motion at the added internal shoulder member 46. FIG. 6 also illustrates the bendable elbow member 47. Both of the bendable sections 46 and 47 provide respective bending motions within the patient (internal of the incision). FIG. 6 also depicts the wrist member 48 which also may be the same as described in U.S. patent application Ser. No. 10/012,845, such as in FIG. 16E through FIG. 16K. The members 47 and 48 may be intercoupled by the forearm member 49. The control cabling that operates the various degrees of freedom couple through the instrument stem 45, and one cable may control the rotation of the forearm member 49. Refer in FIG. 6 to the motion R3 indicating bending at the elbow bendable section 47 and the motion R4 indicating rotation of the forearm member 49 which, in turn, rotates the end effector 50.

In FIG. 6 there are also illustrated motions associated with the wrist 48 and end effector 50. Motion R5 indicates yaw rotation by bending at the wrist member 48. The motions R6 and R7 are remotely controlled at the end effector pivot axis to provide instrument pitch and grip (opening and closing of the end effector jaws).

In the above embodiments, the bendable sections have been described as each providing only a single degree of freedom, or in other words bending in only one direction. However, these bendable sections can also be provided with two degrees of freedom each. In this regard refer, for example, to co-pending U.S. patent application Ser. No. 10/299,588 and the embodiment shown in FIGS. 41-47, and the associated description on page 45 of co-pending U.S. patent application Ser. No. 10/299,588 indicating the two degree of freedom motion at the bendable section, usually, but not necessarily, orthogonal to each other. Refer to page 45 of U.S. patent application Ser. No. 10/299,588 at lines 10-16. FIGS.

16I-16K of U.S. patent application Ser. No. 10/012,845 also shows a bendable section having two degrees of freedom of motion.

Figure 7:
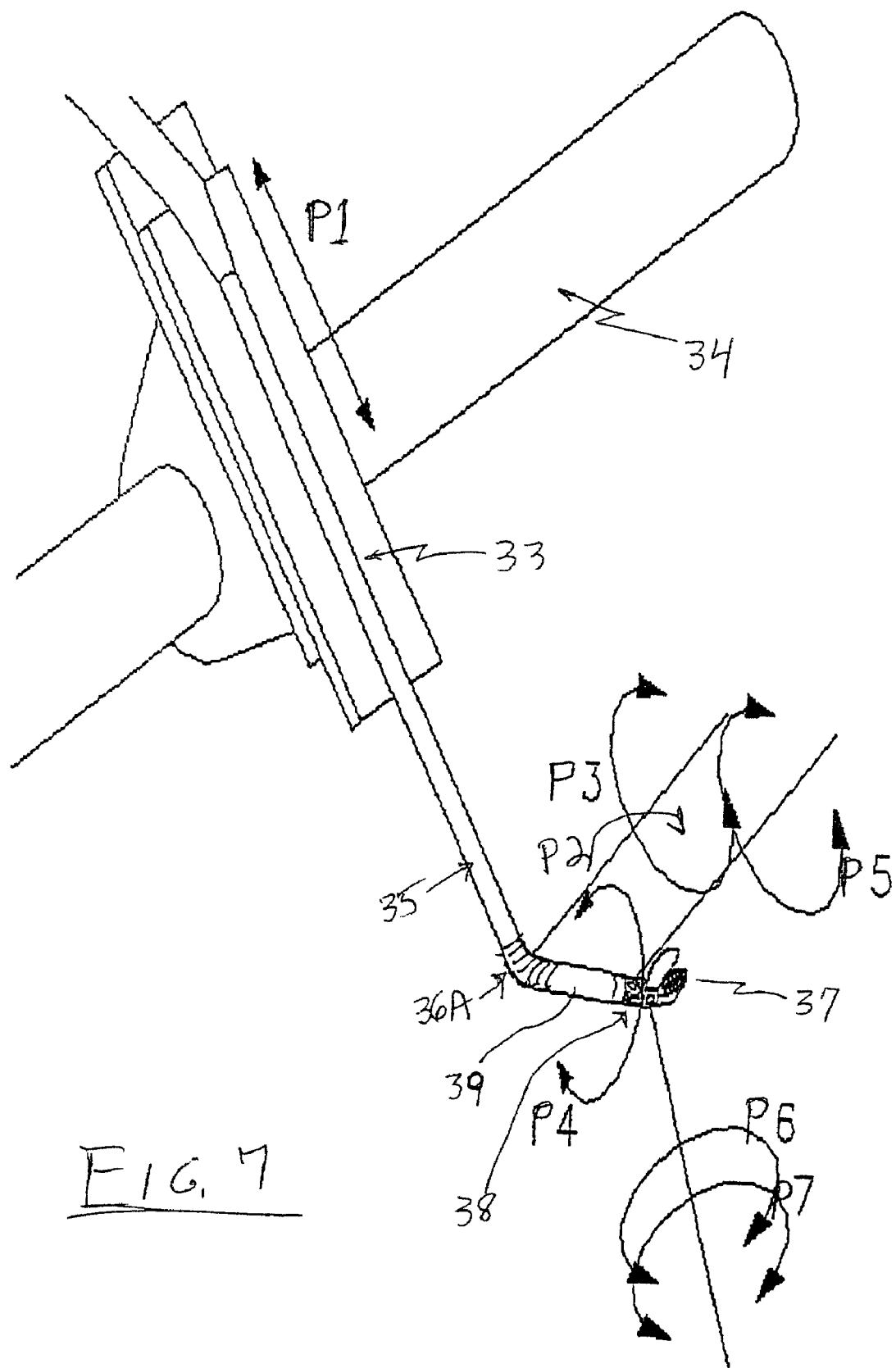
FIG. 7 is a view like that depicted in FIG. 5 but using a bendable section with two degrees of freedom.

Regarding the use of bendable sections with two degrees of freedom, in the embodiment of FIG. 5 such a bendable section may be used for the member 36. In this case, the motion P2 may be replaced by the two degree of freedom member 36, so that there is only translation motion P1 and no rotation motion P2. In this regard refer to FIG. 7 for an illustration of the elbow member 36A having two degrees of freedom depicted as motions P2 and P3. These motions P2 and P3 are usually orthogonal to each other, but could also be at transverse angles other than 90 degrees to each other. In FIG. 7 the same reference numbers are used to identify similar parts found in FIG. 5. The two degree of freedom bendable member 36A is advantageous in that the motion at the incision is further minimized, thus further reducing the chance of stress at the incision. Also, the wrist member 38 may be a bendable two degree of freedom member to provide additional control of the end effector.

Figure 8:
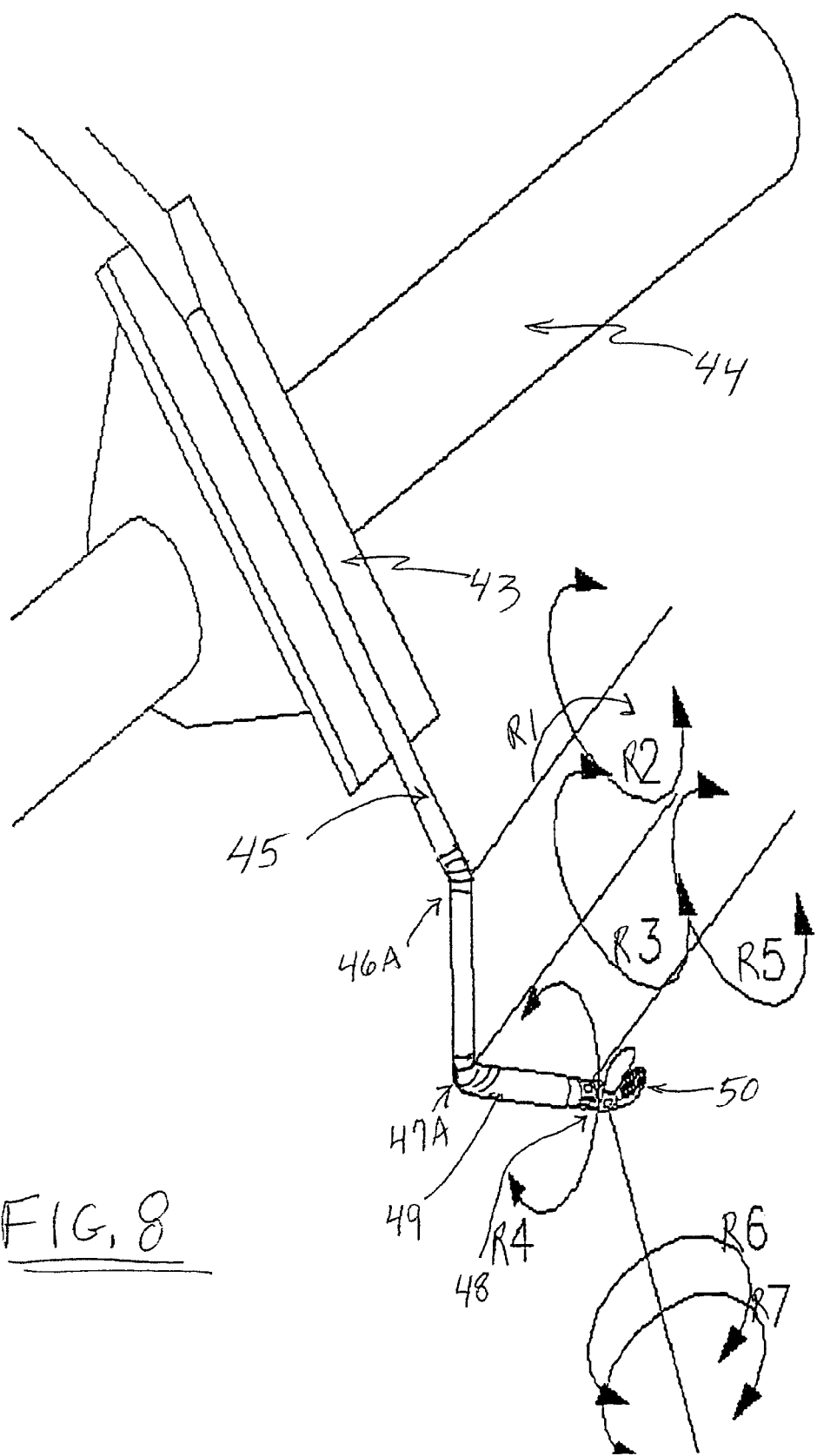
FIG. 8 is a view like that depicted in FIG. 6 but using bendable sections with two degrees of freedom.

In connection with the embodiment described in FIG. 6, this also may be constructed with one or more of the bendable sections as two degree of freedom sections. Moreover the wrist member 48 may also be constructed as a two degree of freedom section. By providing one or more of the members 46 and 47 as two degree of freedom bendable sections, it is even possible to eliminate the rotational motion R1 at the incision, as depicted in FIG. 6. This would further reduce stress at the incision. In this regard refer to FIG. 8 for an illustration of the elbow member 46A having two degrees of freedom depicted as motions R1 and R2. These motions R1 and R2 are usually orthogonal to each other, but could also be at transverse angles other than 90 degree to each other. In FIG. 8 the same reference numbers are used to identify similar parts found in FIG. 6. In the embodiment depicted in FIG. 8 it is noted that there are no motions at the incision, neither translational nor rotational. In FIG. 8 the member 47A may have either one or two degrees of freedom. The rotating arm 49 may be optional. The wrist member 48 may be a pivot wrist, a one degree of freedom bendable section, or a two degree of freedom bendable section.

Thus, the present invention provides a concept whereby at least two internally disposed members are provided, each having a minimum of 1 degree of freedom, simulating "wrist" and "elbow" action in controlling the tool or end effector, and that can be either a "joint" (pivot connection) or "bendable section". Herein, the term "turnable member" is adopted as a generic term intended to cover both pivot joints and bendable sections.

In the embodiments depicted in, for example, FIGS. 5-8 some of the motions may be redundant. An effective instrument can be provided that uses fewer than the degrees of freedom illustrated. For example, in the embodiment of FIG. 5 both the stem 35 and forearm member 39 are described as being controllably rotatable. However, an instrument can be made in which either one of the stem 35 and forearm member 39 is rotatable while the other is not. Particularly when using two degree of freedom members can one possibly eliminate a rotatable shaft member. In another example, in FIG. 8, the forearm member 49 may be non-rotatable.

In accordance with still another aspect of the invention there is provided an adaptor for an instrument that combines both adaptor and instrument into one instrument system that is releasably attached with the instrument base, such as with the instrument carriage or slider. In this regard refer to U.S. patent application Ser. No. 10/012,845 and, for example, FIG. 11 where the instrument insert 16 has been fully inserted into the adaptor 15, particularly into the guide tube 17. Also refer to U.S. patent application Ser. No. 10/302,804 a copy of another filed application showing the detachability of the adaptor for replacement thereof. Refer, for example, to FIG. 16A in U.S. patent application Ser. No. 10/302,804 showing the adaptor 49 and the instrument insert 56. In U.S. patent application Ser. No. 10/302,804 the instrument insert is meant to be insertable and retractable from the adaptor. In an alternate embodiment, the adaptor is detachable, such as in the manner depicted in U.S. patent application Ser. No. 10/302,804, but the instrument insert is coupled permanently with the adaptor so that the instrument insert is no longer inserted and retracted from the guide tube. In such as arrangement the structure can be substantially the same as that described in U.S. patent application Ser. No. 10/302,804, the only difference being that the instrument in no longer meant to be withdrawn from the guide tube. Instead, the adaptor and instrument are formed as a unit and the detachability is at the location where the adaptor is separable from the base or carriage, as depicted in U.S. patent application Ser. No. 10/302,804 in FIG. 16A.

Reference can also be made to other portions of co-pending U.S. patent application Ser. No. 10/299,588, U.S. patent application Ser. No. 10/012,845 and U.S. patent application Ser. No. 10/302,804 for illustrations of other structures usable in controlling the instruments shown in FIGS. 1-8 herein. These co-pending U.S. patent applications particularly U.S. patent application Ser. No. 10/012,845 and U.S. patent application Ser. No. 10/302,804 give clear detail as to the structures that are used in providing the motions illustrated in FIGS. 1-8. This included, inter alia, teachings of cabling through the instrument for controlling joints or bendable sections, specific carriage or slider arrangements for linear translation, instrument and adaptor couplers with interlocking wheel members, and other structures for carrying out the motions depicted.

While this invention has been particularly shown and described with references to preferred embodiments thereof, it will be understood by those skilled in the art that various changes in form and details may be made therein without departing from the scope of the invention encompassed by the appended claims.

What is claimed is:

1. A surgical instrument system comprising:
an instrument member having an instrument shaft and a distal portion positionable through an incision, formed during a minimally invasive procedure performed on a patient, to an internal site and for operation by a surgeon from outside the patient;
a plurality of control cables extending within proximal and distal portions of the instrument shaft;
a motor array coupled to the plurality of control cables;
a tool carried at the distal portion of the instrument member controlled by the surgeon in performing the minimally invasive procedure at an operative site of the patient by manipulation of at least one control cable; and
a wrist member, an elongated rigid forearm member located proximally of the wrist member, and a flexible elbow member located proximally of the elongated rigid forearm member, the wrist member, the elongated rigid forearm member and the flexible elbow member being disposed along the distal portion of the instrument member and controllable with respective control cables, respective distal ends of respective control cables terminating at different respective axial locations within the distal portion of the instrument shaft such that the motor array is operable to drive respective control cables and control movement of the tool, the wrist member, the elongated rigid forearm member and the flexible elbow member, the flexible elbow member being controllably movable with multiple degrees of freedom, the distal portion of the instrument member controllable by the surgeon from outside the patient to pivot and rotate the tool about the wrist member without actuation of the tool, and to pivot the elongated rigid forearm member about the flexible elbow member, wherein the flexible elbow member and the wrist member are spaced apart, separated by the elongated rigid forearm member extending there between, and positioned relative to a distal end of the distal portion so that both the flexible elbow member and the wrist member can be inserted through the incision and into the patient to allow movement of the flexible elbow and wrist members without causing additional trauma to the incision.

2. The surgical instrument system of claim 1 further comprising a user interface including an input device manipulable by the surgeon to control the wrist member, the rigid forearm, the flexible elbow member, and the tool.

3. The surgical instrument system of claim 2 wherein the user interface is located at a master station area remote from the instrument member.

4. The surgical instrument system of claim 1 further comprising a slider supporting the instrument member and controllable by the surgeon from outside the patient to linearly translate the instrument member.

5. The surgical instrument system of claim 4 wherein the slider is controllable by the surgeon from outside the patient to rotate the instrument member about a longitudinal axis of the instrument member.

6. The surgical instrument system of claim 4 further comprising a bracket to which the linear slider is mounted.

7. The surgical instrument system of claim 6 further comprising a rail connectable to a patient bed, wherein the bracket is mounted to the rail.

8. The surgical instrument system of claim 1 wherein the distal portion of the instrument member is controllable by the surgeon from outside the patient to rotate the forearm member about a longitudinal axis of the forearm member relative to the instrument shaft.

9. The surgical instrument system of claim 1 wherein the tool includes opposing jaw members controllable by the surgeon from outside the patient to alternately open and close the jaw members.

10. The surgical instrument system of claim 1 further comprising a rigid arm member and a flexible shoulder member disposed along the distal portion of the instrument member, the distal portion of the instrument member controllable by the surgeon from outside the patient to pivot the arm member about the flexible shoulder member.

11. The surgical instrument system of claim 10, the flexible shoulder member comprising alternating ribs and slots.

12. The surgical instrument system of claim 10, the flexible shoulder member being bendable with two degrees of freedom.

13. The surgical instrument system of claim 1 wherein the forearm member is shorter than the instrument shaft.

14. The surgical instrument system of claim 1, the flexible elbow member comprising alternating ribs and slots.

15. The surgical instrument system of claim 1, the flexible elbow member being bendable in orthogonal directions.

16. The surgical instrument system of claim 1, the wrist member comprising a wrist joint.

17. The surgical instrument system of claim 1, the wrist member comprising a flexible wrist member.

18. The surgical instrument system of claim 17, the flexible wrist member being bendable with two degrees of freedom.

19. The surgical instrument system of claim 17, the flexible wrist member comprising alternating ribs and slots.

20. The surgical instrument system of claim 17, the flexible wrist member being movable with multiple degrees of freedom.

21. A surgical instrument system comprising:
an instrument member having an instrument shaft and a distal portion positionable through an incision, formed during a minimally invasive procedure performed on a patient, to an internal site and for operation by a surgeon from outside the patient;
a plurality of control cables extending within proximal and distal portions of the instrument shaft;
a motor array coupled to the plurality of control cables;
a tool carried at the distal portion of the instrument member controlled by the surgeon in performing the minimally invasive procedure at an operative site of the patient;
a wrist member having multiple degrees of freedom;
an elongated rigid forearm member located proximally of the wrist member; and
an elbow member located proximally of the elongated rigid forearm member, having multiple degrees of freedom and disposed along the distal portion of the instrument member,
respective control cables extending within the instrument shaft, respective distal ends of respective control cables terminating at different respective axial locations within the distal portion of the instrument shaft such that the motor array is operable to drive respective control cables and control movement of the tool, the wrist member, the elongated rigid forearm member and the elbow member, the distal portion of the instrument member being controllable by the surgeon from outside the patient to pivot the tool about the wrist member without actuation of the tool, and to pivot the elongated rigid forearm member about the elbow member, wherein the elbow member and the wrist member are spaced apart, separated by the elongated rigid forearm member extending there between, and positioned relative to a distal end of the distal portion so that both the elbow member and the wrist member can be inserted through the incision and into the patient to allow movement of the elbow and wrist members without causing additional trauma to the incision.

22. The surgical instrument system of claim 21, further comprising a rigid arm member and a shoulder member having multiple degrees of freedom disposed along the distal portion of the instrument member.

* * * * *